United States Patent [19]

Kline

[11] Patent Number: 5,649,900

[45] Date of Patent: Jul. 22, 1997

[54] ANATOMICALLY DESIGNED WRIST SUPPORT

[75] Inventor: Samuel C. Kline, Virginia Beach, Va.

[73] Assignee: Pro/Tec Products, Limited

[21] Appl. No.: 340,872

[22] Filed: Nov. 15, 1994

[51] Int. Cl.$^6$ ............................................. A61F 5/00
[52] U.S. Cl. ..................... 602/21; 602/20; 125/879
[58] Field of Search ................... 482/44, 47; 473/62;
2/159, 161.1, 161.4, 162, 166–168; 213/201,
205, 212, 213; 602/9, 20, 21, 64, 5; 128/878,
879

[56] References Cited

U.S. PATENT DOCUMENTS

| | | | |
|---|---|---|---|
| 3,944,220 | 3/1976 | Fasano | 482/44 |
| 4,584,993 | 4/1986 | Nelson | 602/21 |
| 4,765,319 | 8/1988 | Finnieston et al. | |
| 4,850,341 | 7/1989 | Fabry et al. | |
| 4,854,309 | 8/1989 | Elsey | |
| 4,915,097 | 4/1990 | West | |
| 5,014,689 | 5/1991 | Meunchen et al. | |
| 5,160,314 | 11/1992 | Peters | 602/21 |
| 5,267,943 | 12/1993 | Dancyger | |
| 5,513,657 | 5/1996 | Nelson | 128/879 |

FOREIGN PATENT DOCUMENTS 9401066 1/1994 WIPO ...................................... 602/21

*Primary Examiner*—Richard J. Apley
*Assistant Examiner*—Kim M. Lee
*Attorney, Agent, or Firm*—Whitham, Curtis, Whitham & McGinn

[57] ABSTRACT

An anatomically molded wrist support for use by persons requiring protection from the effects of vibration and repetitive motion is described. The support is comprised of one or more stays and a means for securing this plurality of stays to a hand of a wearer in a wrap-around manner. On the palm side of the support, the stays are used to provide a bias for a slight dorsiflexed position of the wrist. The stays are splayed or flared outwardly towards the palm engaging end to provide a broader region of support. The stays are preferably positioned inside pockets in a wrap-around wrist support.

18 Claims, 2 Drawing Sheets

ANATOMICALLY DESIGNED WRIST SUPPORT

BACKGROUND OF THE INVENTION

1. Field of the Invention

The present invention generally relates to an anatomically designed wrist support which is comprised of one or a plurality of stays and a means for securing this plurality of stays to a hand of a wearer. The wrist support manufactured according to this invention biases the hand towards an optimized wrist gripping position and provides a resistance to wrist motion. Splinting the wrist position in extension provides maximal protection of the median nerve from external vibratory trauma and pressure from between the digital flexor tendons and transverse carpal ligament. The wrist support preferably is tailored to the work environment with a lightweight version for light industrial/clerical applications and a heavier version with antivibrational material for applications when high impact or vibratory tools are used. The wrist support is designed to prevent and treat carpal tunnel syndrome or flexor tenosynovitis. It also has application as a flexible but supportive splint for many forms of mechanical and non-specific wrist pain.

2. Description of the Prior Art

There have been various protective splints which are made to protect the wearer from the detrimental effects of vibration and repetitive motion. For example, U.S. Pat. No. 5,267,943 issued to Dancyger is directed to a flexible elastic adjustable wrist and hand support device. In Dancyger, a plurality of stays are positioned in elongated longitudinal pockets of a wrap-around glove and serve the function of providing resistance against flexure of the wrist and overextension of the wrist. U.S. Pat. No. 5,160,314 to Peters also deals with a technology in this field. It shows an orthotic device comprising a one-piece support for providing pain relief and stabilization in the carpal area. It is designed to anatomically conform to the shape of the wrist at the carpal area. A removable palmar stabilizing stay which can be bent to the contour of the hand contributes to this objective. U.S. Pat. No. 4,854,309 to Elsey discloses a flexible wrist splint which can be used while working and is useful in the treatment of cumulative trauma disorder. Elements of the splint include a flexible panel adapted to encircle the wrist area and two opposed pockets to contain flexible and resilient stays.

However, problems in connection with universal wrist splints still exist in that prior art technologies fail to effectively deal with vibratory trauma and cumulative trauma of repetitive motion inducing and aggravating carpal tunnel syndrome and flexor tenosynovitis. Existing wrist splints are often uncomfortable since they cut into the hand and forearm with attempted wrist flexion. Sometimes they require immobilization of the hand and wrist for their stabilization. By contrast, the splint of the present invention is unique in that it provides flexible support for the wrist in the extended position.

SUMMARY OF THE INVENTION

The invention uniquely addresses the problems of carpal tunnel syndrome and flexor tenosynovitis in a safe and efficacious manner. Wrist extension is important to protect the median nerve from vibratory trauma. Studies have shown that the median nerve is several millimeters farther from the palm of the hand and transverse carpal ligament when the wrist is extended. When the wrist is in neutral or flexion, the nerve not only rests on the transverse carpal ligament but is compressed between the ligament and the flexor tendons which use the transverse carpal ligament to prevent tendon bowstringing when the wrist is flexed. This is especially significant in the patient with carpal tunnel syndrome since the nerve may be densely adherent to the underside of the transverse carpal ligament. Therefore, nerve position is a critical factor in preventing direct vibratory trauma to the nerve and forcible compression by the flexor tendons.

It is therefore an object of this invention to provide a wrist support that protects the wearer from the detrimental effects of vibration and repetitive motion.

It is another object of this invention to provide a wrist support that allows a functional range of motion while maintaining optimal wrist position.

It is still another object of this invention to provide a wrist support that contains a vibration absorbing material.

A wrist support in this invention fits around a wearer's wrist in a wrap-around manner. The support is preferably made of a synthetic material or leather and includes a thumb passage and securing means for holding the support on the wrist. One or a plurality of stays are positioned on the palm side of the hand, and the stays provide a wrist extensor bias across the entire surface of the hand.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENTS OF THE INVENTION

Figure 1:
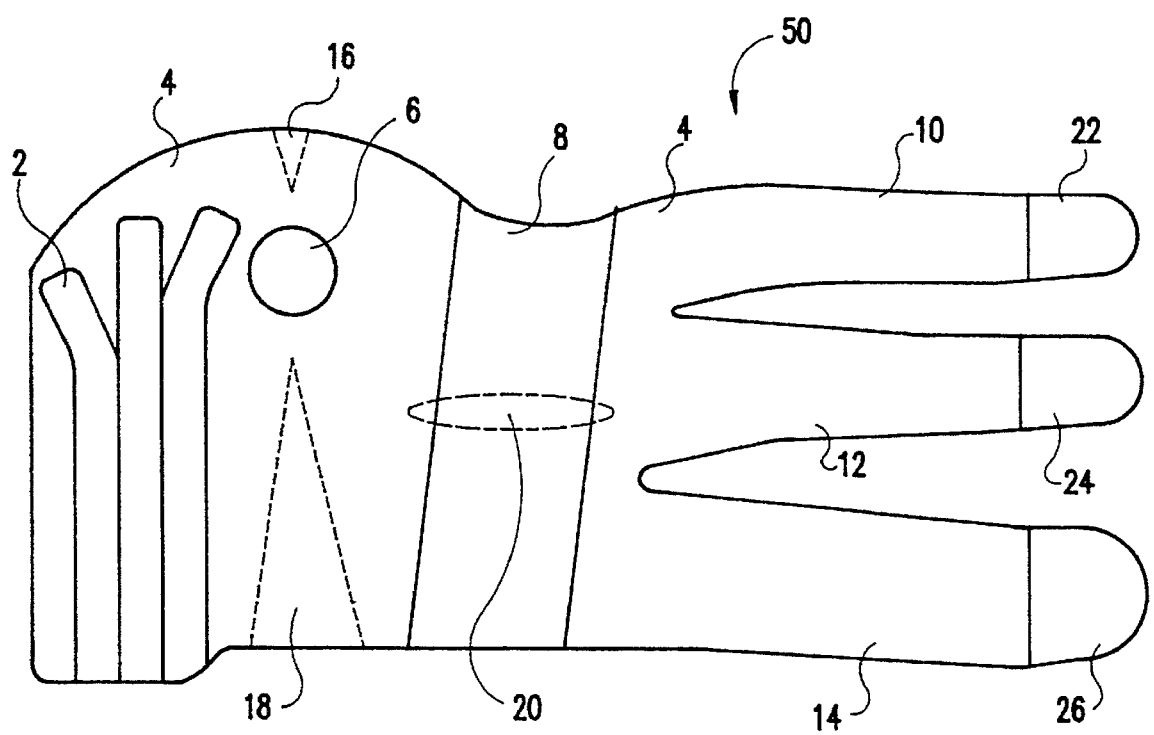
FIG. 1 is a top view of the wrist support of the present invention in an unwrapped configuration.

Referring now to the drawings, and more particularly to FIG. 1, there is a wrist support 50 according to the present invention in an unwrapped configuration.

The wrist support 50 preferably includes pockets 2 augmented with anatomically molded stays 30, a thumb passage 6, and fastening means 8, 22, 24, 26 for holding the wrap-around element on the wrist. The support 50 can be made from neoprene, an oil-resistant synthetic rubber made by polimerization of chloroprene. Neoprene provides vibration absorbing properties to the support 50. However, it should be understood that the material used for the support 50 can vary widely within the practice of this invention. For example, leather, rubber, cordura, ansotex, ballistic nylon, pack cloth, canvas, and a wide variety of fabrics may be used. In some applications, the wrist support will be worn underneath a glove. In this application, the material for the support 50 will ideally be made from a very thin material. Further, using neoprene with more absorbent underlining such as terry cloth has an advantage of increased absorption of vibration.

Figure 2A:
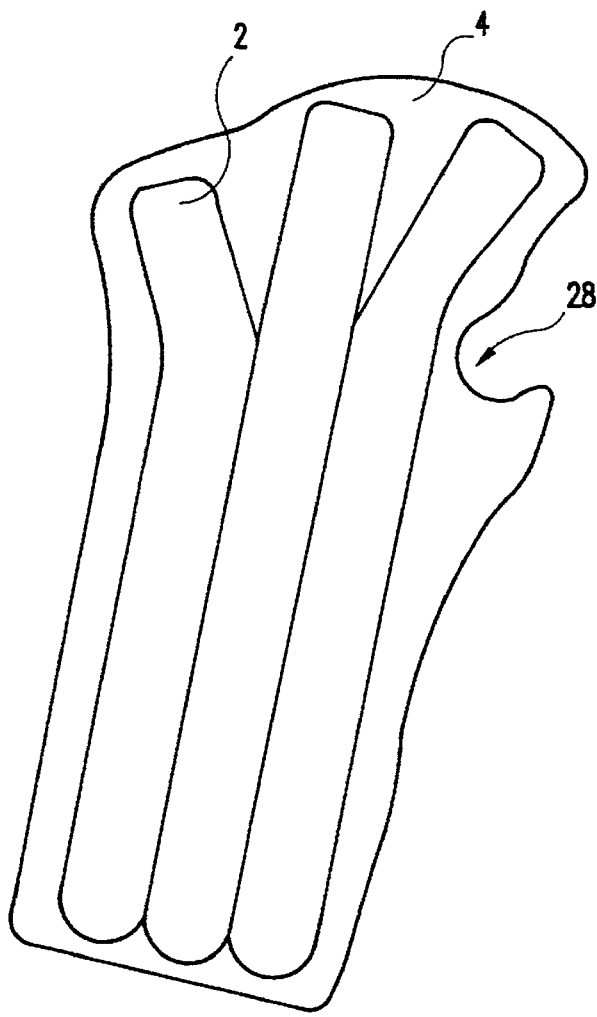
FIG. 2a is a cross-sectional top view of the pockets of the support in which the stays are positioned.
Figure 3A:
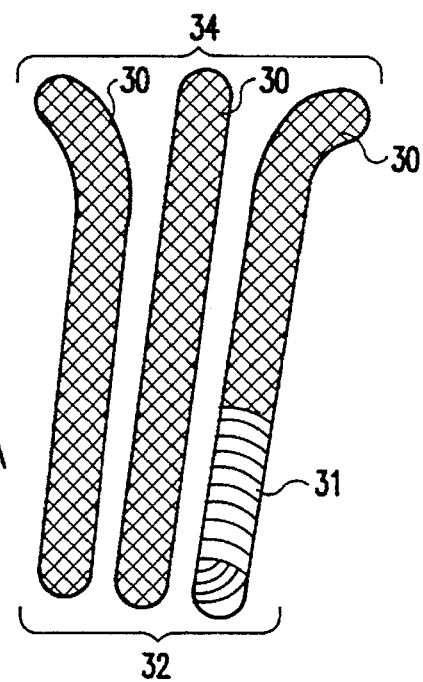
FIG. 3a is a front view of the stays showing their outwardly splayed configuration to provide support across the entire surface of the hand.

On the palm side of the support 50, three metal stays 30, shown uncovered in FIG. 3a but contained in pockets 2 in FIGS. 1 and 2a, are used to provide a bias for a slight dorsiflexed position of the wrist. The stays 30 are preferably positioned inside pockets 2 made of the same or different material as the support 50 itself. The stays 30 are made from a material which is rigid enough to restrict wrist motion and bias the hand of a wearer for wrist extension; however, the stays 30 must be flexible enough to allow comfortable wrist movement, and resilient so that they can return to the biased position. Recommended materials for the stays 30 can vary widely and include metals and molded plastics. In one embodiment, the stay can have a spiral or coiled configuration 3 along its length as is shown at the base of the stay on the right in FIG. 3a. The stays 30 should be light weight and thin so that they do not impose a burden to a wearer. For example, preferably the stays 30 should have a weight on the order of less than 2–3 ounces and a thickness on the order of fractions of an inch less than ¼".

An important aspect of this invention is that the user is able to close Ms or her hand without pain or annoyance. In this regard, the stays 30 should not be so long that they advance up the wrist to a place and Where closing the hand causes the stays 30 to dig into the arm. Ideally, the stays 30 will be of a length sized to advance 1 to 3 inches past the wrist so that the "dig-in" problem is minimized or avoided.

Each of the stays 30 have a wrist-engaging section 32 and a palm-engaging section 34. FIG. 3a shows the stays 30 at the wrist-engaging section 32 are positioned together in a side-by-side fashion so that they accommodate the relatively narrower wrist region and to minimize the "dig-in" problem in the hand. Preferably, the total width of the three stays at wrist engaging end 32 ranges between 1 and 2 inches. FIG. 3a also shows that the stays 30 at the palm-engaging section 34 are spread apart and flared outwardly across the palm to cover a broader region of support for the entire hand. FIGS. 1, 2a, and 3 show that this out-flaring occurs at approximately one fourth of a length of the stays 30. Preferably the area supported by the palm-engaging section 34 is 1.2 times the area supported by the wrist-engaging section 32 or greater. For example, good results have been achieved with the stays 30 having a total width at wrist engaging end of approximately 1.75 inches and a total width at palm engaging end 34 of approximately 2.25 inches.

Figure 3B:
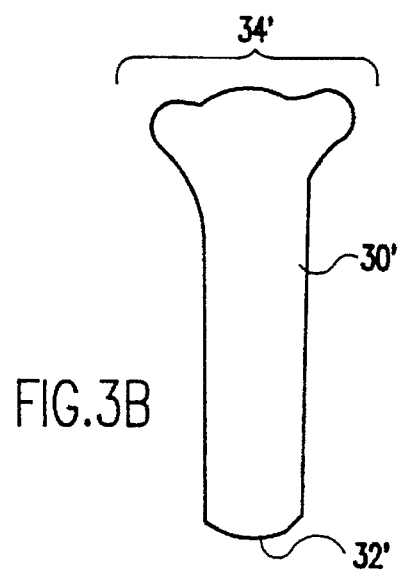
FIG. 3b is a front view of a single stay which incorporates the outwardly splayed configuration to provide support across the entire surface of the hand.

Ideally three stays are used in the practice of this invention; however, the number of stays can be one or more as long as they provide a broad region of support for the whole hand. For example, FIG. 3b shows a single stay 30' which has a wide palm engaging section 34' and a narrow wrist engaging section 32', whereby the "dig-in" problem discussed above is minimized by limiting the length of the stay 30' and the width of the stay 30' at the wrist engaging end 32'. The stay 30' could be-placed inside a pocket of a glove, or otherwise secured to a wrist support.

Figure 2B:
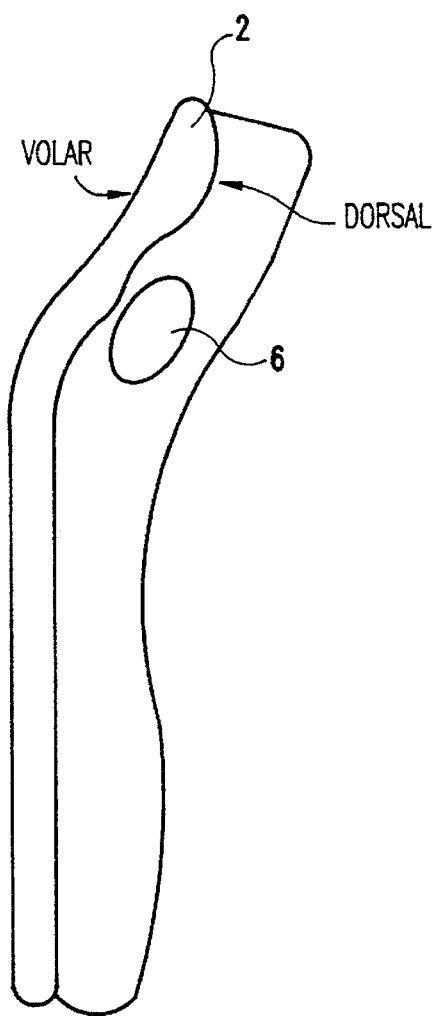
FIG. 2b is a side view of the wrist support showing the bend in the stays at the palmar region.

FIG. 2b shows an important element of this invention wherein each of the stays 30 has a bend 36 along its length. The bend 36 is designed to bias the wrist in extension, which is the position of the greatest grip strength, as well as to allow wrist flexion without discomfort. The bend 36 is directed into the palm of a hand and is preferably of an angle ranging from 20° to 40°, and most preferably approximately 30°. Because of this bend 36, the stays 30 rest on the palm of a hand comfortably along the contour of the hand, especially the intersection area of the palm and the wrist. The bend 36 should occur at a region along the length of the stays 30 that allows for gripping by the hand. FIG. 2b shows that the bend 36 occurs at approximately one third of a length of the stays 30.

FIG. 2a shows pockets 2 made of the same or different material as the support 50 itself as well as cut-away portions 28 at the site of a thumb passage 6. As discussed above with respect to the support 50, it is preferably that the material be resistant to abrasion. For example, the material can be canvas, cordura, ansotex, leather, ballistic nylon, pack cloth, or the like. Preferably the stays 30 shown in FIG. 3a are sewn into the pockets 2; however, it is also possible to have the stays 30 insertable and removable by the wearer.

Another embodiment of the present invention involves the use of a vibration absorbing material positioned at a site adjacent to the plurality of the stays, at either the volar or dorsal side to maximize the vibration damping effect. A suitable material for absorbing vibration would be neoprene, sorbathane, M Plus, or the like. Alternatively, light-weight anti-vibration materials can be used or eliminated in another embodiment for office settings.

Figure 4:
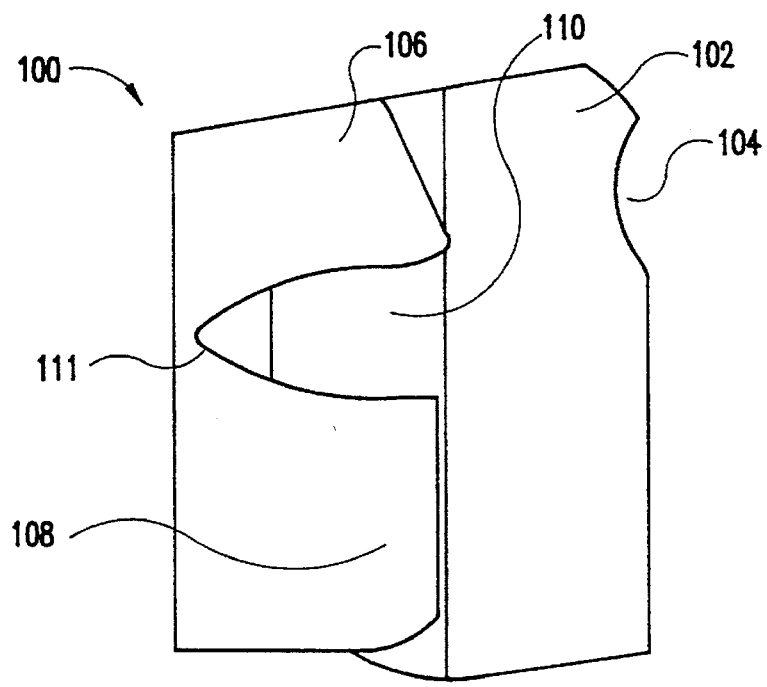
FIG. 4 is a back view of a wrist support of the present invention which utilizes two strap connectors.

FIG. 1 shows the support 50 is preferably secured to the hand with contact hook and pile fastening means such as VELCRO available from Du Pont (see connector section 8 and fasteners 22, 24, and 26). Likewise, FIG. 4 shows the use of VELCRO fastening along the back side of the wrap around support 100. While the use of VELCRO is a preferred material in this invention and is a matter of design choice, any means for easy and speedy fastening of the wrap-around element, such as snap connectors and hooks, can be used.

With respect to FIG. 1, connector section 8 is integral with the wrap-around element 4. At the tip portions of the fastening straps 10, 12, 14 are fasteners 22, 24, 26, respectively, that are securable to the connector section 8. The first strap 10 preferably passes between the thumb and index finger as it is wrapped around the wearer's hand. Location of strap 10 at this site may help to support the wrist in mild dorsiflexion. The remaining two straps 12 and 14 secure the support 50 to the wrist. FIG. 1 shows three fastening straps 10, 12, and 14; however, it should be understood that there can be greater or fewer number of straps to secure the wrap-around element to the hand. The advantage of having three fastening straps is that they can be spread apart over the wrist and hand to provide a superior anatomical fit for fight and comfortable fastening of the wrap-around element 4.

The portions 16, 18, 20 are devised to enhance anatomic fit. An ellipse of material is removed from the dorsal wrist section in the connector section 8 at location 20 to allow the wrap-around element 4 to mold and match the dorsiflexed bend of the stays 30. Darts 16 and 18 remove additional material above and below the thumb passage 6 to accommodate the thumb region of the hand. Thus, the support 50 is sewn together along the dashed lines at darts 16 and 18. As long as the wrap-around element fits in tightly and comfortably around the hand, both a thumb passage and darts may not be required. Alternatively, only the thumb passage or only one dart may be necessary for tight fastening of the wrap-around element, or more than two darts may be required in another embodiment, or the thumb passage may be modified to be a cut-away portion, or a web strap can be added for the thumb.

With particular reference to FIG. 4, an alternative wrist support 100 design includes a wrap around body 102 preferably made of abrasion resistant material such as leather, canvas, cordura, ansotex, ballistic nylon, pack cloth, or the like, which includes a thumb passage 104, and a pair of connector straps 106 and 108 that are secured to a pile region 110 on the back of the support 100. The wrist support 100 design of FIG. 4 is uncomplicated and easily applied to the hand by the wearer. Positioning the V-shaped cutout 111 between straps 106 and 108 in line with the thumb passage 104 allows the wrist support 100 to readily adapt to the contours of the hand in the wrist extended position as described above in conjunction with FIG. 2b.

It is also contemplated that the design of the wrist support can be modified and refined in several ways. For example, a more durable material, such as leather, can be positioned on the volar surface of the support to provide the support with enhanced durability. The wrist support can also include ventilation holes. In particular, the wrist support could be fabricated from a fenestrated or meshed material to allow for improved ventilation. Further, special leather gloves with cut-outs or additional material sewn over knuckles and the wrist allow full digital flexion when wearing over an anti-vibration wrist support. While FIGS. 1 and 4 contemplate a "half-glove" design, it is also contemplated that a full glove which would cover the fingers of the wearer could also employ the stay supports described in conjunction with FIGS. 2a–b and 3a–b.

In addition to its unique design configuration, the support of the present invention is anticipated to have many applications. The support can be used in the working environment by workers who use high-impact or vibratory tools. A lightweight version without antivibration material can be made for use in light industrial or clerical applications including typing, key boarding, and light assembly line duties, etc. The wrist support can be used prophylactically for preventing carpal tunnel syndrome and flexor tenosynovitis. It would also be useful as a treatment for individuals who are recovering from these conditions. It would also be beneficial to patients who have already had carpal tunnel surgery and who return to the use of vibratory tools since the nerve is even more vulnerable to vibratory trauma.

While the invention has been described in terms of a single preferred embodiment, those skilled in the art will recognize that the invention can be practiced with modification within the spirit and scope of the appended claims.

Having thus described my invention, what I claim as new and desire to secure by Letters Patent is as follows:

1. A wrist support, comprising:
    a plurality of stays, each of said stays having a wrist engaging section and a palm-engaging section along a length dimension, each of said stays having a bend located between said wrist engaging section and said palm engaging section along said length dimension, said bend having an angle ranging from 20° to 40° relative to said wrist engaging section to bias a user's hand toward wrist extension, each of said stays are made from a material which is rigid enough to reduce wrist motion and bias said hand for wrist extension, but which is flexible enough to allow wrist flexion of said hand; and
    means for securing said plurality of stays to a hand, each of said stays being oriented adjacent one another with said bend in each stay being angled towards a palm of said hand, at least a first stay of said plurality of stays having said palm engaging section flared outward from said wrist engaging section towards a radial side of said hand and at least a second stay of said plurality of stays having said palm-engaging section flared outward from said wrist engaging section towards and ulnar side of said hand.

2. The wrist support of claim 1 wherein said material is a metal.

3. The wrist support of claim 1 wherein said material is a plastic.

4. The wrist support of claim 1 wherein said material is oriented in a spiral form along said length dimension.

5. The wrist support of claim 1 further comprising an anti-vibration material positioned adjacent to said plurality of stays.

6. The wrist support of claim 5 wherein said anti-vibration material is located on a volar side of said stays.

7. The wrist support of claim 5 wherein said anti-vibration material is located on a dorsal side of said stays.

8. The wrist support of claim 5 wherein said anti-vibration material is selected from the group consisting of neoprene, sorbothane, and IMPLUS.

9. The wrist support of claim 1 wherein said means for securing said plurality of stays to said hand comprises a wrist wrap which wraps around said hand, and means for fastening said wrist wrap to said hand after it has been wrapped around said hand.

10. The wrist support of claim 9 wherein said means for fastening includes hook and pile fasteners.

11. The wrist support of claim 9 wherein said wrist wrap includes a plurality of cut-outs and darts to conform to the hand and wrist in the extended position.

12. The wrist support of claim 9 wherein said wrist wrap includes a durable material which covers a volar side of said wrist support.

13. The wrist support of claim 12 wherein said durable material is abrasion resistant and is selected from the group consisting of cordura, ansotex, ballistic nylon and pack cloth.

14. The wrist support of claim 9 wherein said wrist wrap includes an absorbent material under said wrist support.

15. A wrist support, comprising:
    at least one stay forming a splay stay support, said splay stay support having both a wrist engaging section and a palm-engaging section along a length dimension wherein said wrist engaging section is of a narrower width relative to said palm-engaging section, said splay stay support having a bend located between said wrist engaging section and said palm engaging section along said length dimension, said bend having an angle ranging from 20° to 40° relative to said wrist engaging section to bias a user's hand toward wrist extension, said splay stay support being made from a material which is rigid enough to reduce wrist motion and bias said hand for wrist extension, but which is flexible enough to allow wrist flexion of said hand; and
    means for securing said splay stay support to a hand, said bend in said splay stay support being angled towards a palm of said hand, said palm engaging end of said splay stay support being flared outwardly towards said radial and ulnar sides of said hand to provide support over the width of said hand.

16. The wrist support of claim 15 wherein said means for securing said splay stay support to said hand comprises a wrist wrap which wraps around said hand, and means for fastening said wrist wrap to said hand after it has been wrapped around said hand.

17. The wrist support of claim 16 wherein said splay stay support is comprised of a single stay.

18. The wrist support of claim 16 wherein said splay stay support is comprised of three stays positioned adjacent one another with a first stay splayed at said palm engaging end towards said radial side of said hand and a second stay splayed at said palm engaging end towards said ulnar side of said hand.

* * * * *